(12) United States Patent
Arakawa et al.

(10) Patent No.: US 12,167,208 B2
(45) Date of Patent: Dec. 10, 2024

(54) EAR MODEL, PERFORMANCE EVALUATION METHOD, AND PERFORMANCE EVALUATION SYSTEM

(71) Applicant: NEC Corporation, Tokyo (JP)

(72) Inventors: Takayuki Arakawa, Tokyo (JP); Yoshitaka Ito, Tokyo (JP)

(73) Assignee: NEC CORPORATION, Tokyo (JP)

( * ) Notice: Subject to any disclaimer, the term of this patent is extended or adjusted under 35 U.S.C. 154(b) by 225 days.

(21) Appl. No.: 17/782,726

(22) PCT Filed: Dec. 13, 2019

(86) PCT No.: PCT/JP2019/048843
§ 371 (c)(1),
(2) Date: Jun. 6, 2022

(87) PCT Pub. No.: WO2021/117205
PCT Pub. Date: Jun. 17, 2021

(65) Prior Publication Data
US 2023/0007418 A1 Jan. 5, 2023

(51) Int. Cl.
*H04R 29/00* (2006.01)
(52) U.S. Cl.
CPC .................. *H04R 29/00* (2013.01)
(58) Field of Classification Search
CPC ........ H04R 29/00; H04R 29/001; H04R 1/46; H04R 2460/13; H04R 2499/11; H04R 25/30; H04R 1/1016; H04R 1/1041; H04R 25/00; H04R 5/027; H04M 1/24; G10K 15/00; G06T 2207/10072; G06T 2207/10081; G06T 7/0012; G06T 7/12

USPC ............... 381/56–58, 600; 600/500
See application file for complete search history.

(56) References Cited

U.S. PATENT DOCUMENTS

| | | | |
|---|---|---|---|
| 5,787,187 A | 7/1998 | Bouchard et al. | |
| 2007/0057941 A1* | 3/2007 | Fang | H04R 25/658 700/118 |
| 2009/0097724 A1* | 4/2009 | McBagonluri | G06V 10/44 382/128 |

(Continued)

FOREIGN PATENT DOCUMENTS

| | | | | |
|---|---|---|---|---|
| CN | 104490491 | * | 1/2017 | ............... A61F 2/18 |
| CN | 104490491 B | | 1/2017 | |

(Continued)

OTHER PUBLICATIONS

Indian Office Action for IN Application No. 202247038769 mailed on Oct. 26, 2022.

(Continued)

*Primary Examiner* — Lun-See Lao
(74) *Attorney, Agent, or Firm* — Sughrue Mion, PLLC

(57) ABSTRACT

[Problem] To evaluate, easily and at low cost, the performance of an earphone device used for ear acoustic certification.
[Solution] Holes are provided in a plurality of plate-shaped members (201), an artificial eardrum member (202) corresponds to the eardrum of an individual, and the holes provided in each of the plurality of plate-shaped members (201) are connected, whereby the plurality of plate-shaped members (201) are layered over the artificial eardrum member (202) so as to simulate the external auditory canal of the individual.

11 Claims, 9 Drawing Sheets

(56) References Cited

U.S. PATENT DOCUMENTS

2015/0256944 A1* 9/2015 Inagaki .................. G01H 17/00
381/60

FOREIGN PATENT DOCUMENTS

| | | |
|---|---|---|
| CN | 110269626 A | 9/2019 |
| JP | 2005-032056 A | 2/2005 |
| JP | 2005-535017 A | 11/2005 |
| JP | 2015-165717 A | 9/2015 |
| JP | 2019-062377 A | 4/2019 |
| KR | 10-2016-0099232 A | 8/2016 |
| WO | 2013/172039 A1 | 11/2013 |
| WO | 2017/069118 A1 | 4/2017 |

OTHER PUBLICATIONS

Extended European Search Report for EP Application No. 19956063.2 dated on Nov. 23, 2022.
International Search Report for PCT Application No. PCT/JP2019/048843, mailed on Feb. 18, 2020.
English translation of Written opinion for PCT Application No. PCT/JP2019/048843, mailed on Feb. 18, 2020.
Christopher M. Bishop, "Pattern Recognition and Machine Learning", Springer Science + Business Media, LLC, Chapter 4, pp. 179-224, Feb. 15, 2010.

* cited by examiner

Fig.5

| ACOUSTIC CHARACTERISTIC DATA | | |
|---|---|---|
| PARAMETERS OF PLATE-SHAPED MEMBER | | DATA OF TRANSFER FUNCTION ($x_i = x_1, x_2, \ldots$) |
| SIZE (R) OF RADIUS OF HOLE | NUMBER (n) OF PLATE-SHAPED MEMBER | |
| 5 [mm] | 1 | |
| 5 [mm] | 2 | |
| 10 [mm] | 3 | |
| 10 [mm] | 4 | |
| 15 [mm] | 5 | |
| 20 [mm] | 6 | |

EAR MODEL, PERFORMANCE EVALUATION METHOD, AND PERFORMANCE EVALUATION SYSTEM

This application is a National Stage Entry of PCT/JP2019/048843 filed on Dec. 13, 2019, the contents of all of which are incorporated herein by reference, in their entirety.

TECHNICAL FIELD

The present invention relates to an ear model, a performance evaluation method, and a performance evaluation system, and particularly relates to a personal authentication technology based on an individual characteristic of a shape of a human ear hole.

BACKGROUND ART

For example, fingerprint authentication, vein authentication, face authentication, iris authentication, and voice authentication have been known as personal authentication technologies (referred to as biometric authentication technologies) based on individual characteristics of living bodies. Among the personal authentication technologies, particularly in-ear acoustic authentication pays attention to individual characteristics of internal structures of human ear holes. In the in-ear acoustic authentication, an inspection signal is input to an ear hole of an individual to be authenticated, and personal authentication is performed using an echo signal based on an echo sound from the ear hole.

The individual (person to be authenticated) to be subjected to the personal authentication wears a device (referred to as an earphone device or a hearable device) having an earphone shape incorporating an in speaker and a microphone on the auricle. The speaker of the earphone device transmits the inspection signal (sound wave) toward the inside of the ear hole of the person to be authenticated. The microphone of the earphone device collects echo sound from the ear hole. Then, an echo signal based on the echo sound is transmitted from the earphone device to a personal authentication device. The personal authentication device performs personal authentication by collating the echo signal received from the earphone device with echo signals of one or a plurality of individuals registered in advance.

The in-ear acoustic authentication technology has advantages that personal authentication is completed instantaneously and stably, that personal authentication can be immediately performed in a state where an individual wears the earphone device (hands-free) even when the individual is moving or working, and that confidentiality regarding an internal structure of a human ear hole is high.

CITATION LIST

Patent Literature

[PTL 1] WO 2017/069118 A
[PTL 2] WO 2013/172039 A
[PTL 3] JP 2005-535017 A

Non Patent Literature

[NPL 1] "PATTERN RECOGNITION AND MACHINE LEARNING" (CHRISTOPHER M. BISHOP) (Springer Science+Business Media, LLC) (Feb. 15, 2010)

SUMMARY OF INVENTION

Technical Problem

In a related in-ear acoustic authentication technology, performance of an earphone device is evaluated. Specifically, a plurality of subjects are caused to wear the same earphone device in order to test in-ear acoustic authentication, and a false rejection rate (FRR) and a false acceptance rate (FAR), which are index values of performance of the earphone device, are calculated. However, it is necessary to restrain the subjects over a long period of time in order to accurately evaluate the performance of the earphone device, and thus, there are problems that time and effort for the performance evaluation are great and that cost is high.

The present invention has been made in view of the above problems, and an object thereof is to provide a technology for evaluating performance of an earphone device to be used for in-ear acoustic authentication easily and inexpensively.

Solution to Problem

An ear model according to one aspect of the present invention includes: a plurality of plate-shaped members provided with holes; and an artificial eardrum member equivalent to an eardrum of an individual, the holes, each of which is provided in each of the plurality of plate-shaped members, being connected, whereby the plurality of plate-shaped members are stacked on the artificial eardrum member in such a way as to simulate an external auditory canal of the individual.

A performance evaluation method according to one aspect of the present invention is a method for evaluating performance of an earphone device to be used for in-ear acoustic authentication using the ear model, and includes: transmitting an inspection signal from the earphone device toward a site of the ear model equivalent to an external auditory canal opening of the individual; collecting echo sound, transmitted from the ear model after the inspection signal propagates in the ear model, using the earphone device; calculating an acoustic characteristic of the ear model from an echo signal based on the collected echo sound; and evaluating performance of the earphone device based on the acoustic characteristic.

A performance evaluation system according to one aspect of the present invention includes: the ear model; an earphone device that transmits an inspection signal from the earphone device toward a site of the ear model equivalent to an external auditory canal opening of the individual and collects an echo sound transmitted from the ear model after the inspection signal propagates in the ear model; and a computing device that calculates an acoustic characteristic of the ear model from an echo signal based on the collected echo sound and calculates an index value indicating performance of the earphone device based on the acoustic characteristic.

Advantageous Effects of Invention

According to one aspect of the present invention, it is possible to easily and inexpensively evaluate the performance of the earphone device to be used for the in-ear acoustic authentication.

BRIEF DESCRIPTION OF DRAWINGS

FIG. 5 is an example of acoustic characteristic data generated by an acoustic characteristic accumulation unit of the computing device according to the first example embodiment.

EXAMPLE EMBODIMENT

First Example Embodiment

A first example embodiment will be described below with reference to FIGS. 1 to 7.
(Performance Evaluation System 1)

Figure 1:
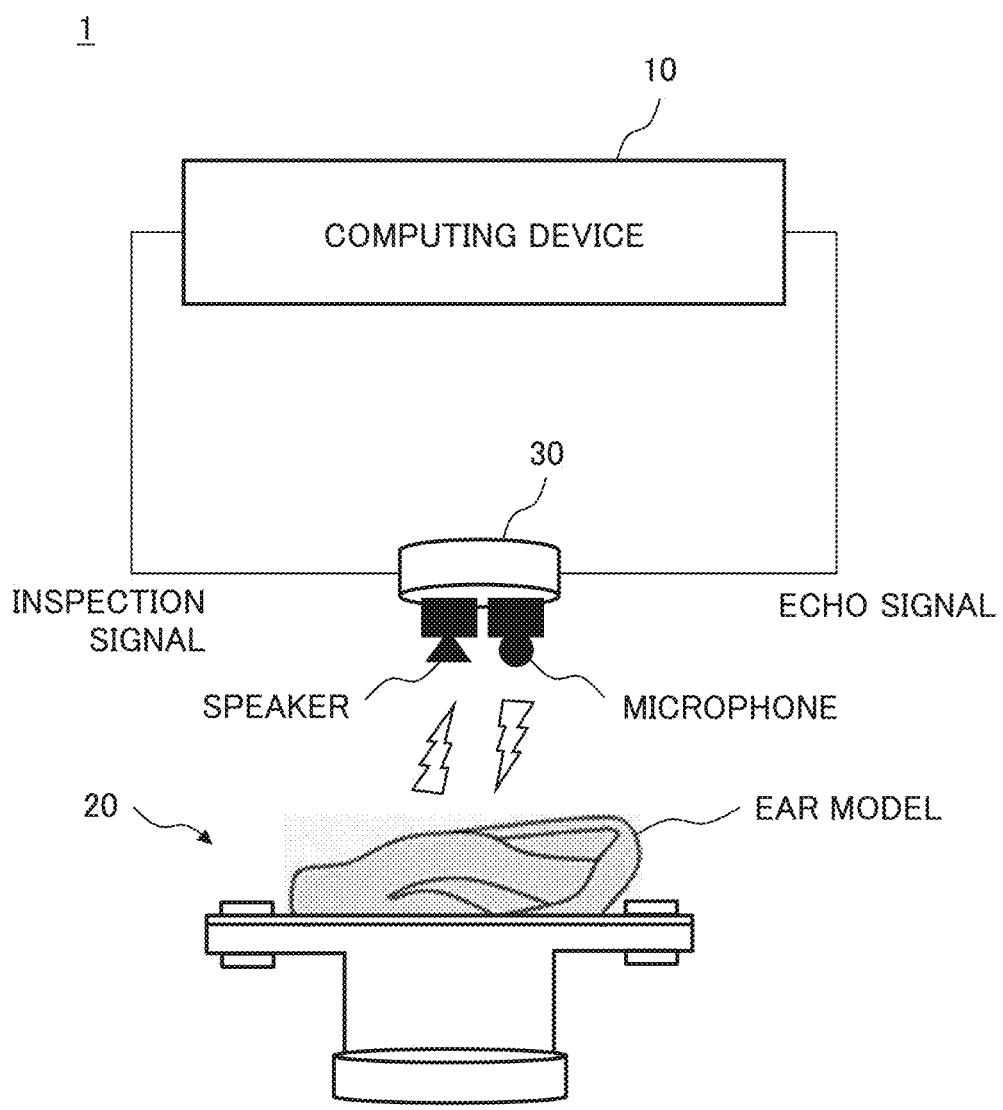
FIG. 1 is a schematic diagram illustrating a configuration of a performance evaluation system according to a first example embodiment.

A configuration of a performance evaluation system 1 according to the first example embodiment will be described with reference to FIG. 1. FIG. 1 is a schematic diagram illustrating the configuration of the performance evaluation system 1. As illustrated in FIG. 1, the performance evaluation system 1 includes a computing device 10, an ear model 20, and an earphone device 30. The performance evaluation system 1 is used to evaluate performance of the earphone device 30.

The computing device 10 reproduces an inspection signal and causes the inspection signal to be transmitted from the earphone device 30 to the ear model 20. Then, the computing device 10 observes an echo signal based on echo sound, transmitted from the ear model 20 after the inspection signal propagates in the ear model 20, and calculates an index value indicating the performance of the earphone device 30 based on the echo signal.

In general, there are two elements in the performance of the earphone device 30. That is, there are a false rejection rate (FRR) and a false acceptance rate (FAR). When the performance of the earphone device 30 is high, both the false rejection rate (FRR) and the false acceptance rate (FAR) are low. In the first example embodiment, the computing device 10 calculates a J value as one index value indicating the performance of the earphone device 30. The J value will be described in detail later.

The ear model 20 simulates an internal structure of an ear hole of an individual. More specifically, the ear model 20 is provided with a hole, and this hole simulates at least the internal structure (hereinafter, referred to as an external auditory canal) from an external auditory canal opening to an eardrum in the ear hole of an individual (the hole of the ear model 20 will be described later). An auricle model is placed on the ear model 20. The auricle model is manufactured to match a shape of the earphone device 30 (FIG. 1). For example, the auricle model is manufactured by taking a mold of an auricle of an individual and pouring a material such as silicone rubber of a fluid into the mold. Alternatively, an auricle of an individual may be scanned to generate 3D data of the auricle, and an auricle model may be manufactured by a 3D printer technology based on the generated 3D data of the auricle.

The earphone device 30 incorporates at least a speaker and a microphone. However, in FIG. 1, the speaker and microphone incorporated in the earphone device 30 are schematically illustrated on the surface of the earphone device 30. The earphone device 30 is attached so as to be embedded in a portion equivalent to an ear hole opening of the auricle model. The earphone device 30 is connected to the computing device 10 in a wireless or wired manner.

The earphone device 30 receives an instruction to transmit the inspection signal from the computing device 10. The earphone device 30 transmits the inspection signal from the speaker incorporated in the earphone device 30 to the inside of the hole of the ear model 20 through an ear hole opening provided in the auricle model. The earphone device 30 collects echo sound, transmitted from the ear model 20 after the inspection signal propagates in the ear model 20, by the microphone. The earphone device 30 generates the echo signal based on the echo sound collected by the microphone and transmits the echo signal to the computing device 10.
(Ear Model 20a)

Figure 2:
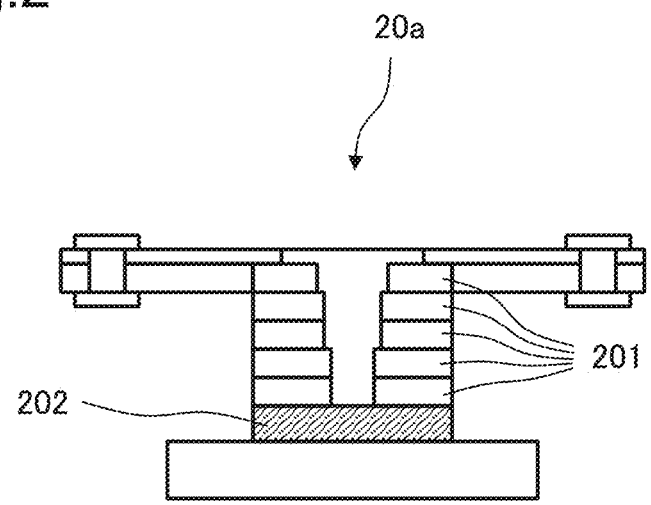
FIG. 2 is a cross-sectional view of an ear model provided in the performance evaluation system according to the first example embodiment.

FIG. 2 is a cross-sectional view of an ear model 20a which is an example of the ear model 20 illustrated in FIG. 1. As illustrated in FIG. 2, the ear model 20a according to the first example embodiment includes at least a plurality of plate-shaped members 201 and one artificial eardrum member 202. FIG. 2 does not illustrate an auricle model (also referred to as an artificial auricle) on the ear model 20a. The plate-shaped member 201 is made of, for example, acrylic. The artificial eardrum member 202 is, for example, a film made of silicon or Teflon.

An upper surface of the ear model 20a illustrated in FIG. 2 corresponds to a surface on which the auricle model is arranged in FIG. 1. A hole of the plate-shaped member 201 located on the uppermost surface of the ear model 20a is equivalent to an external auditory canal opening of an individual. An internal structure (specifically, an external auditory canal) of an ear hole of an individual is simulated by connecting holes provided at centers of the plurality of plate-shaped members 201 from the upper surface of the ear model 20a (the surface in contact with the auricle model) to the artificial eardrum member 202. The plurality of plate-shaped members 201 are stacked and accommodated in a hollow cylinder. In the hollow cylinder, the plate-shaped member 201 on the upper side is in close contact with the plate-shaped member 201 on the lower side (or the artificial eardrum member 202) by its own weight and the weight of the plate-shaped member 201 on the upper side thereof.

Figure 3:
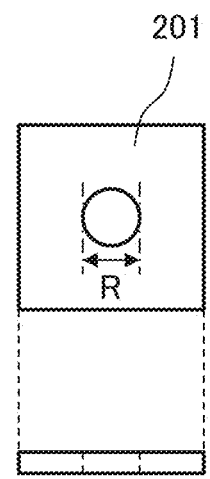
FIG. 3 is a view illustrating a shape of a plate-shaped member provided in the ear model according to the first example embodiment.

FIG. 3 illustrates a shape of the plate-shaped member 201 forming the ear model 20a. As illustrated in FIG. 3, the hole penetrating through the plate-shaped member 201 in the thickness direction is provided at the center of the plate-shaped member 201. A thickness of the plate-shaped member 201 is, for example, 5 mm. A size (R) of a diameter of the hole is variable, for example, between 5 mm and 20 mm. The plate-shaped member 201 is made of, for example, acrylic.

However, a material of the plate-shaped member 201 is not particularly limited. In general, acoustic characteristics of the ear hole depend on a length and a thickness, but do not depend on the complexity of the curvature of the ear hole. An acoustic characteristic of the ear hole do not depend on a material or texture (hardness) of an inner wall of the ear hole. Therefore, even if the ear model 20a is formed using the plate-shaped member 201 having a material or texture different from that of a human ear, or even if the plurality of plate-shaped members 201 are linearly arranged, the acoustic characteristic substantially equivalent to those of an ear hole of an individual having the same length and thickness as those of the hole of the ear model 20a.

In the ear model 20a, the plurality of plate-shaped members 201 are stacked in an arrangement order according to the number (n) assigned to each of the plate-shaped members 201 in advance. The sizes (R) and arrangement orders (n) of the holes of the plurality of plate-shaped members 201 are determined based on an internal structure of an ear hole of an individual to be simulated by the ear model 20a.

The thicknesses and the number of the plurality of plate-shaped members 201 constituting the ear model 20a are related to a length from the external auditory canal opening to the eardrum of the individual (simulated by the internal structure of the hole of the ear model 20a).

The size of the diameter of the hole provided in each of the plurality of plate-shaped members 201 forming the ear model 20a are related to the thickness of the external auditory canal of the individual (simulated by the internal structure of the hole of the ear model 20a).

Data on the internal structure of the ear hole of the individual is obtained by, for example, computed tomography (CT) scanning. In this case, parameters (R, n) of the ear model 20a may be obtained from a result of executing the CT scan on a subject.

In one example, three-dimensional data of an external auditory canal of the subject may be displayed on a display to request a worker to input the parameters (R, n) of the ear model 20a. In another example, the computing device 10 analyzes the result of executing the CT scan to determine the parameters (R, n).

(Application Examples)

Note that the performance evaluation system 1 can also be applied to a speech communication device other than the earphone device 30. For example, the performance evaluation system 1 evaluates performance of a headphone device covering an auricle model, instead of the earphone device 30. In this case, a speaker and a microphone may be provided in an ear-contact portion of the headphone device. In another application example, the performance evaluation system 1 can also evaluate performance of a telephone device in which a speaker and a microphone are provided in a portion equivalent to a receiver, instead of the earphone device 30.

(Computing Device 10)

Figure 4:
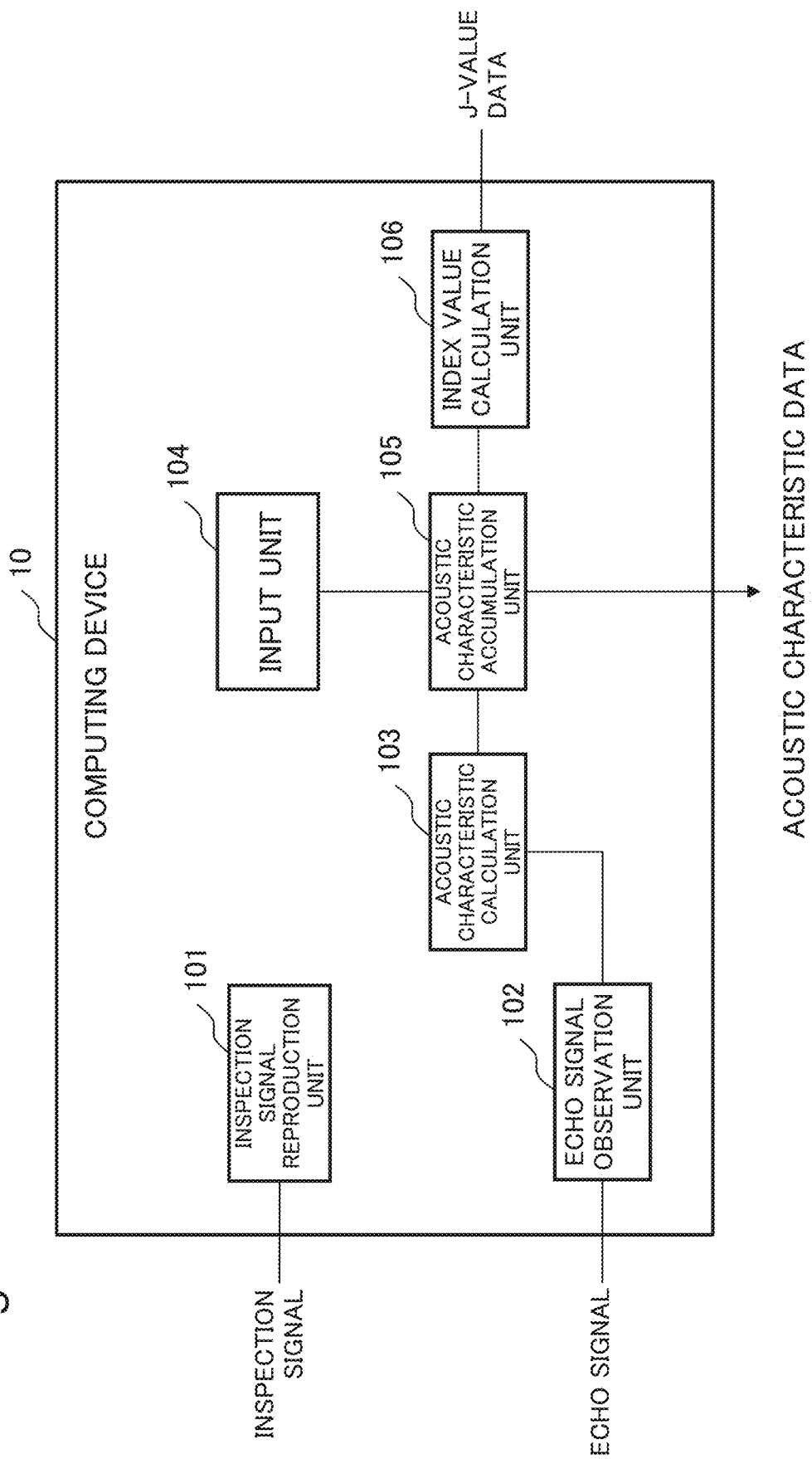
FIG. 4 is a block diagram illustrating a configuration of a computing device according to the first example embodiment.

A configuration of the computing device 10 according to the first example embodiment will be described with reference to FIG. 4. FIG. 4 is a block diagram illustrating a configuration of the computing device 10. As illustrated in FIG. 4, the computing device 10 includes an inspection signal reproduction unit 101, an echo signal observation unit 102, an acoustic characteristic calculation unit 103, an input unit 104, an acoustic characteristic accumulation unit 105, and an index value calculation unit 106.

The inspection signal reproduction unit 101 reproduces an inspection signal to be input to the ear model 20a. The inspection signal input to the ear model 20a echoes inside a hole of the ear model 20a, and echo sound is output from the ear model 20a. Data obtained by encoding the inspection signal reproduced by the inspection signal reproduction unit 101 is stored in advance in a recording medium (not illustrated). The inspection signal reproduction unit 101 acquires the data of the inspection signal stored in the recording medium, and reproduces the inspection signal. How to determine the inspection signal is not particularly limited. For example, the inspection signal is experimentally determined based on general thickness and length of ear holes of a plurality of individuals such that echo sound from the ear hole of any individual is strong (or S/N is large).

The echo sound indicates a characteristic depending on an internal structure of the hole of the ear model 20a (referred to as an acoustic characteristic of the ear model 20a). The acoustic characteristic of the ear model 20a is equivalent to an acoustic characteristic of an ear hole of an individual simulated by the hole of the ear model 20a. Since an internal structure of an ear hole of an individual has individuality, it is possible in principle to identify the individual based on the acoustic characteristic of the ear hole of the individual.

The inspection signal reproduction unit 101 transmits the reproduced inspection signal to the earphone device 30 in a wireless or wired manner, and causes the inspection signal to be output from the speaker of the earphone device 30. Specifically, the inspection signal is an impulse wave.

The echo signal observation unit 102 observes the echo signal based on the echo sound from the ear model 20a using the microphone of the earphone device 30. More specifically, the echo sound is output from the ear model 20a after the inspection signal propagates in the ear model 20a. The microphone of the earphone device 30 collects the echo sound output from the ear model 20a. The earphone device 30 converts the echo sound collected by the microphone into digital data to generate the echo signal.

The echo signal observation unit 102 requests the echo signal from the earphone device 30. The earphone device 30 transmits the echo signal to the echo signal observation unit 102 in a wireless or wired manner. The echo signal observation unit 102 receives the echo signal from the earphone device 30 in a wireless or wired manner. The echo signal observation unit 102 transmits the echo signal received from the earphone device 30 to the acoustic characteristic calculation unit 103.

The acoustic characteristic calculation unit 103 receives the echo signal from the echo signal observation unit 102. The acoustic characteristic calculation unit 103 calculates a transfer function as the acoustic characteristic of the ear model 20a from the received echo signal. That is, the transfer function is an example of the acoustic characteristic. A response function based on a response (echo signal) of the ear model 20a to the inspection signal is another example of the acoustic characteristic.

Specifically, the acoustic characteristic calculation unit 103 first extracts an impulse response from the echo signal. The impulse response is a response (echo signal) of the ear model 20 with respect to the inspection signal that is the impulse wave. The acoustic characteristic calculation unit 103 performs Fourier transform or Laplace transform on the impulse response to calculate the transfer function. The acoustic characteristic calculation unit 103 transmits data of the calculated transfer function to the acoustic characteristic accumulation unit 105.

The input unit 104 acquires information indicating the size (R) of the diameter of the hole provided at the center of each of the plate-shaped members 201 (FIG. 4) and a number of each of the plate-shaped members 201, that is, the arrangement order (n) as the parameters of the ear model 20*a*. For example, the input unit 104 requests a user to input the size (R) of the diameter of the hole provided in each of the plurality of plate-shaped members 201 and the arrangement orders of the plate-shaped members 201 by display, sound, or other means.

The input unit 104 analyzes an input operation of the user with respect to the computing device 10 to acquire information indicating the parameters (R, n) of the ear model 20*a*. The input unit 104 transmits the information indicating the parameters (R, n) of the ear model 20*a* to the acoustic characteristic accumulation unit 105.

The acoustic characteristic accumulation unit 105 receives the data of the transfer function from the acoustic characteristic calculation unit 103. The acoustic characteristic accumulation unit 105 receives the information indicating parameters (R, n) of the ear model 20*a* from the input unit 104. The acoustic characteristic accumulation unit 105 accumulates the data of the transfer function received from the acoustic characteristic calculation unit 103 in the recording medium (not illustrated) as acoustic characteristic data in association with information indicating the parameters (R, n) of the ear model 20*a* (here, the first flow ends).

Thereafter, the worker detaches the earphone device 30 from the ear model 20*a* and attaches the same earphone device 30 to the same ear model 20*a* again (the second flow starts from here). The computing device 10 acquires the acoustic characteristic data again by the above-described procedure. As the acoustic characteristic data is repeatedly acquired this manner, it is possible to evaluate how much reproducibility the earphone device 30 has with respect to attachment and detachment to and from the single ear model 20*a*, that is, how much the acoustic characteristic data with little variation can be acquired.

Hereinafter, a flow ID: i (i=1, 2, . . . ) is introduced to distinguish the transfer function acquired in the first flow from transfer functions acquired in the second and subsequent flows. The computing device 10 stores data (x$_i$) of the acoustic characteristic obtained in the i-th flow and the parameters (R, n) in the recording medium in association with each other. The above procedure is repeated a predetermined plurality of times. Thereafter, the acoustic characteristic accumulation unit 105 transmits the acoustic characteristic data (that is, the transfer function (x$_i$) (i=1, 2, . . . ) and the parameters (R, n)) accumulated in the recording medium to the index value calculation unit 106. As above, the data of the transfer function (x$_i$) (i=1, 2, . . . ) has been collected using the single ear model 20*a* (more specifically, the ear model 20*a* having the same parameters).

Subsequently, the worker attaches the earphone device 30 to another ear model (hereinafter, referred to as another ear model 20*a*) having parameters (R, n) different from those of the ear model 20*a* described above. Here, the parameters (R, n) of the another ear model 20*a* is different from the parameters (R, n) of the ear model 20*a* described above. The computing device 10 acquires the transfer functions (x$_i$) for a predetermined plurality of times by the above-described procedure, and stores a set of the parameters (R, n) and the transfer functions (x$_i$) for the predetermined plurality of times in the recording medium in association with each other.

Hereinafter, the plurality of ear models 20*a* having different parameters (R, n) are distinguished by ear model IDs: g=1 to G (>1). The ear model 20*a* assigned with the ear model ID: g is sometimes described as "ear model 20*a* (ear model ID: g)".

FIG. 5 is an example of the acoustic characteristic data stored in the recording medium by the acoustic characteristic accumulation unit 105. As illustrated in FIG. 5, the acoustic characteristic data includes the parameters (R, n) of the ear model 20*a* and the transfer function (x$_i$) (i=1, 2, . . . ). As described above, the parameters (R, n) are the size (R) of the diameter of the hole of the plate-shaped member 201 and the number (n) of the plate-shaped member 201. The acoustic characteristic accumulation unit 105 generates the acoustic characteristic data illustrated in FIG. 5 for each of the plurality of ear models 20*a* having the different parameters (R, n).

The index value calculation unit 106 receives the acoustic characteristic data illustrated in FIG. 5 from the acoustic characteristic accumulation unit 105. The index value calculation unit 106 calculates an index value indicating performance of the earphone device 30 using the received acoustic characteristic data. Specifically, the index value calculation unit 106 calculates V$_B$ and the V$_W$ according to the following formulas.

[Formula 1]

$$V_B = \sum_{g=1}^{G} n_g \{\mu_g - \mu\}\{\mu_g - \mu\}^T \qquad (1)$$

[Formula 2]

$$V_W = \sum_{g=1}^{G} \sum_{i=g}^{n_g} \{y_i - \mu_g\}\{y_i - \mu_g\}^T \qquad (2)$$

Here, in Formula (2), bold y$_i$ (i=1, 2, . . . ) is a vector (referred to as output vector) representing an output when a predetermined input is received by a system of the ear model 20*a* (ear model ID: g) having the transfer function (x$_i$) (i=1, 2, . . . ) and the earphone device 30. The number of measurements related to one ear model 20*a* (ear model ID: g) is represented by n$_g$ (g=1 to G). An average value of output vectors regarding one ear model 20*a* (ear model ID: g) is represented by μ$_g$. An average value of μ$_g$ (g=1 to G) regarding all the ear models 20*a* (ear model IDs: 1 to G) is represented by p. T represents transposition of the vector. In addition, "i: =g" of the second sigma in Formula (2) indicates that i is a variable and g is fixed.

In Formula (1), V$_B$ is obtained by summing variances of the average values μ$_g$ (g=1 to G) of the output vectors regarding the system in which one ear model 20*a* (ear model ID: g) and the earphone device 30 are integrated for all the ear models 20*a* (ear model IDs: 1 to G). V$_B$ varies depending on how the earphone device 30 is attached to the ear model 20*a*, and V$_B$ also varies depending on characteristics, arrangement, volume, and the like of the speaker and the microphone of the earphone device 30. The earphone device 30 with larger V$_B$ is preferable in terms of identification of the ear model 20*a* (and identification of an individual). V$_B$ relates to a false acceptance rate (FAR) indicating first performance of the earphone device 30.

In Formula (2), V$_W$ relates to the system in which one ear model 20*a* (ear model ID: g) and the earphone device 30 are integrated. In Formula (2), the variance of the output vectors (bold y$_i$) (i=1, 2, . . . , n$_g$) obtained by n$_g$ flows is obtained, and the sum of the variance is obtained for all the ear models 20*a* (ear model IDs: g=1 to G). V$_W$ varies depending on how the earphone device 30 is attached to the ear model 20*a*, and this variance also varies depending on characteristics, arrangement, volume, and the like of the speaker and the microphone of the earphone device 30. The earphone device 30 with smaller $V_W$ is preferable in that a success rate (or non-authentication rate) of personal authentication can be made constant. $V_W$ relates to a false rejection rate (FRR) indicating second performance of the earphone device 30. Hereinafter, $V_B$ is sometimes referred to as (the sum of) inter-model variance, and $V_W$ is sometimes referred to as (the sum of) intra-model variance.

The index value calculation unit 106 calculates the following J value using the inter-model variance $V_B$ and the intra-model variance $V_W$. The J value indicates a characteristic of a system in which the earphone device 30 and the ear model 20a are regarded as the integrated system. The larger the J value is, the higher the accuracy with which the computing device 10 correctly identifies the ear model 20a.

Strictly speaking, when a combination of the earphone device 30 and the ear model 20a (or an individual) is different, the inter-model variance $V_B$ and the intra-model variance $V_W$ are different. However, as long as the inter-model variance $V_B$ and the intra-model variance $V_W$ are obtained for the ear models 20a of a sufficient number of samples G and the ear models 20a are equivalent to ear holes of individuals with various attributes (for example, age, sex, race, height, and the like), it is considered that such a large difference is not generated in the inter-model variance $V_B$ and the intra-model variance $V_W$ even if some ear models 20a are replaced with other ear models. In that case, as long as the accuracy with which the computing device 10 identifies a certain ear model 20a (or certain individual) is high, it can be expected that the identification accuracy for another ear model 20a (or another individual) is also high.

Therefore, it is possible to measure the inter-model variance $V_B$ and the intra-model variance $V_W$ for combinations of the earphone device 30 and several ear models 20a (or several individuals), and evaluate whether the earphone device 30 is suitable for the purpose of identifying a large number of ear models 20a (or a large number of individuals) based on the magnitude of the following J value.

[Formula 3]

$$J(\omega) = \frac{V_B}{V_W} \quad (3)$$

The J value is a function of a frequency ω. The J value is called an evaluation function in Fisher's linear discriminative analysis (LDA) (for example, PTL 3 and NPL 1). According to Formula (3), the larger the inter-model variance $V_B$, the larger the J value. The smaller the intra-model variance $V_W$, the larger the J value. The large inter-model variance $V_B$ means that accuracy of an identification function of the ear model 20a by the earphone device 30 is high. The small intra-model variance $V_W$ means that the variation in accuracy with which in-ear acoustic authentication succeeds is small even if the same earphone device 30 is repeatedly attached to and detached from the same ear model 20a. Therefore, it can be said that the earphone device 30 having a high J value has high performance.

(Performance Evaluation Method)

Figure 6:
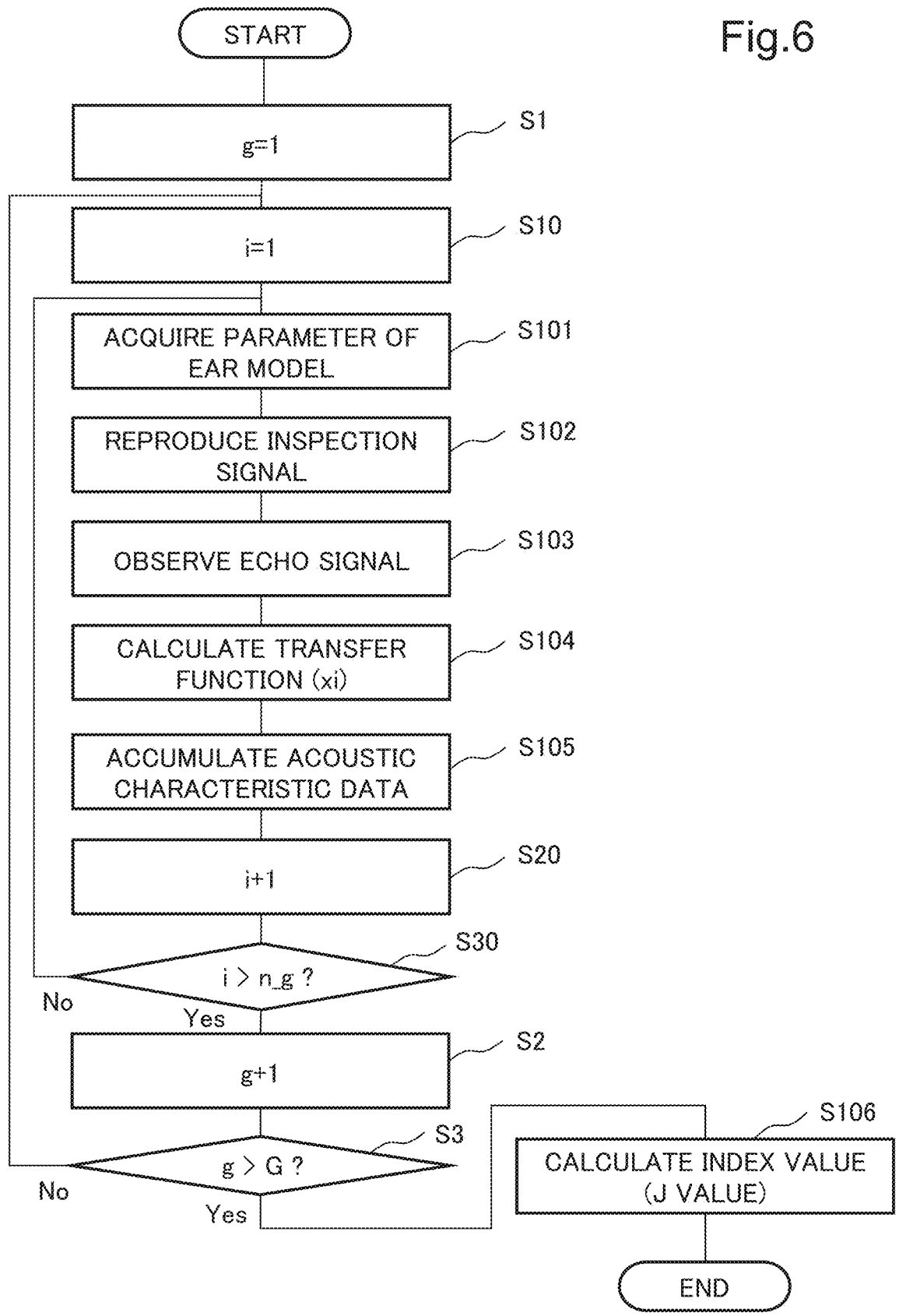
FIG. 6 is a flowchart illustrating an operation of the computing device according to the first example embodiment.

A performance evaluation method executed by the computing device 10 of the performance evaluation system 1 according to the first example embodiment will be described with reference to FIG. 6. FIG. 6 is a flowchart illustrating a flow of the performance evaluation method.

As illustrated in FIG. 6, first, a first variable g and a second variable i are set in the performance evaluation method (S1, S10). The first variable g indicates the above-described ear model ID. The second variable i is a flow ID for identifying a plurality of measurements.

The input unit 104 acquires parameters (R, n) of the ear model 20a (ear model ID; g) (S101). The input unit 104 transmits information indicating the acquired parameters (R, n) to the acoustic characteristic accumulation unit 105.

The inspection signal reproduction unit 101 reproduces an inspection signal to be input to a hole of the ear model 20a (S102).

The inspection signal reproduction unit 101 transmits the reproduced inspection signal to the earphone device 30 (FIG. 1) in a wireless or wired manner. The inspection signal reproduction unit 101 causes the reproduced signal to be transmitted from a speaker of the earphone device 30. The speaker incorporated in the earphone device 30 transmits the inspection signal toward the hole of the ear model 20a.

A microphone of the earphone device 30 collects echo sound from the ear model 20a. The earphone device 30 converts the collected echo sound into digital data to generate an echo signal. Then, the earphone device 30 transmits the echo signal to the computing device 10 in a wireless or wired manner.

Returning to FIG. 6, the echo signal observation unit 102 of the computing device 10 observes the echo signal based on the echo sound from the ear model 20a (S103). Specifically, the echo signal observation unit 102 receives the echo signal generated from the echo sound in a wireless or wired manner from the earphone device 30.

The acoustic characteristic calculation unit 103 calculates an acoustic characteristic of the ear model 20a based on the received echo signal (S104). Specifically, the acoustic characteristic calculation unit 103 calculates a transfer function, obtained by performing Fourier transform or Laplace transform on an impulse response, as the acoustic characteristic of the ear model 20a. The acoustic characteristic calculation unit 103 transmits data of the calculated transfer function ($x_i$) to the acoustic characteristic accumulation unit 105.

The acoustic characteristic accumulation unit 105 receives the data of the transfer function ($x_i$) from the acoustic characteristic calculation unit 103. The acoustic characteristic accumulation unit 105 receives the parameters (R, n) of the ear model 20a from the input unit 104. The acoustic characteristic accumulation unit 105 accumulates the acoustic characteristic data ($x_i$) received from the acoustic characteristic calculation unit 103 in a recording medium (not illustrated) as acoustic characteristic data (FIG. 5) in association with the information indicating the parameters (R, n) (S105).

Thereafter, one is added to the above-described second variable (flow ID) i (S20). When the second variable i is equal to or less than $n_g$(No in S30), the flow returns to step S101. At this time, a worker detaches the earphone device 30 from the ear model 20a and attaches the same earphone device 30 to the same ear model 20a again. Here, the same ear model 20a means the ear models 20a having the same parameters (R, n), and thus, is not necessarily one specific ear model 20a.

When the second variable i exceeds $n_g$ (Yes in S30), one is added to the first variable g (ear model ID) (S2). In this case, the flow proceeds to step S3. In FIG. 6, "$n_g$" is written as "n_g". At this time, the worker detaches the earphone device 30 from the ear model 20a, and attaches the earphone device 30 to another ear models 20a having different parameters (R, n).

When the first variable g does not exceed G (No in S3), the flow returns to step S10. When the first variable g exceeds G (Yes in S3), the acoustic characteristic accumulation unit 105 transmits the acoustic characteristic data accumulated in the recording medium to the index value calculation unit 106.

The index value calculation unit 106 receives the acoustic characteristic data from the acoustic characteristic accumulation unit 105. The index value calculation unit 106 calculates a J value, which is one index value indicating performance of the earphone device 30, according to the above-described Formula (3) using the received acoustic characteristic data (S106). The flow of the performance evaluation method ends as above.

(Evaluation Result of Performance of Earphone Device 30)

Figure 7:
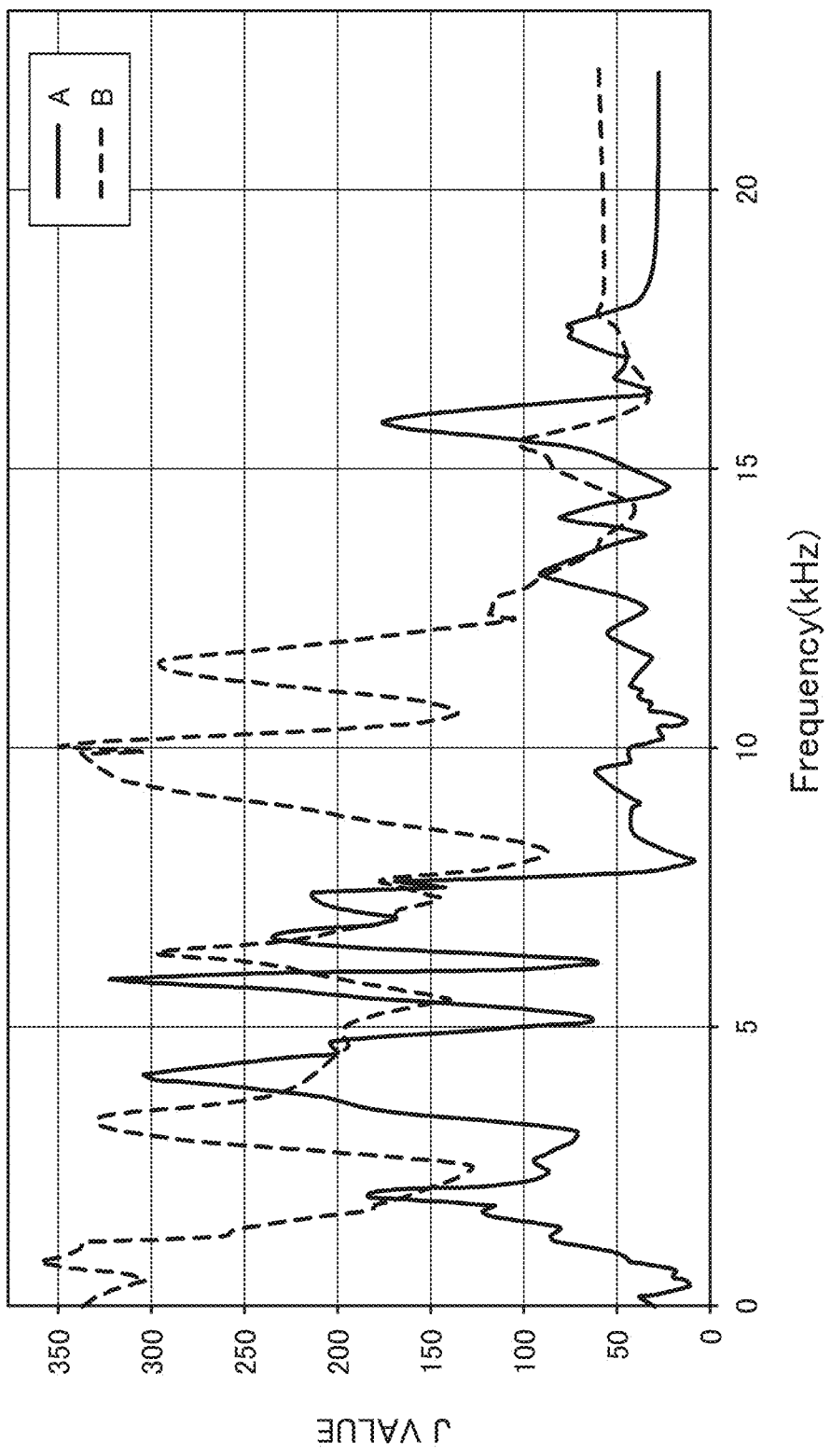
FIG. 7 is a graph illustrating an evaluation result (J value) of performance of an earphone device by the performance evaluation system according to the first example embodiment.

FIG. 7 illustrates an evaluation result of performance of the earphone device 30 by the computing device 10. FIG. 7 illustrates an example of a J value which is an index value calculated by the index value calculation unit 106. FIG. 7 illustrates graphs of the J values regarding two earphone devices 30 (A and B). According to FIG. 7, the earphone device (B) has the larger J value in a frequency band of 10 kHz and its vicinity than that of the earphone device (A). That is, it can be said that the earphone device (B) has higher performance than the earphone device (A) at least in this frequency band. A reason why a difference between the J value of the earphone device (A) and the J value of the earphone device (B) is large in an extremely low frequency band (near 0 kHz) is that a normal speaker has a small output in the extremely low frequency band that is inaudible to humans, so that an echo sound is weak, and the influence of noise on the weak echo sound is relatively large.

Effects of Present Example Embodiment

According to the configuration of the present example embodiment, the plurality of plate-shaped members 201 are provided with holes, the artificial eardrum member 202 is equivalent to an eardrum of an individual, and the holes, each of which is provided in each of the plurality of plate-shaped members 201, are connected, whereby the plurality of plate-shaped members 201 are stacked on the artificial eardrum member 202 so as to simulate an external auditory canal of the individual. The earphone device 30 is attached to the ear model 20a, and the in-ear acoustic authentication is tried to evaluate the performance of the earphone device 30. The ear models 20a having various parameters (R, n) can be easily obtained by changing sizes of diameters of the holes provided in the plurality of plate-shaped members 201 and arrangement orders of the plurality of plate-shaped members 201. As a result, it is possible to easily and inexpensively evaluate the performance of the earphone device 30 to be used for the in-ear acoustic authentication.

Second Example Embodiment

A second example embodiment will be described with reference to FIG. 8.

(Ear Model 20b)

Figure 8:
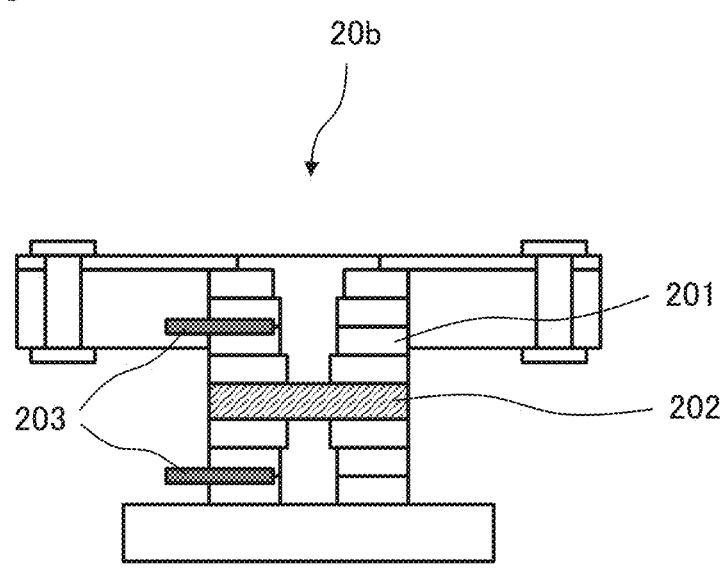
FIG. 8 is a cross-sectional view of an ear model according to a second example embodiment.

FIG. 8 is a cross-sectional view of an ear model 20b which is an example of the ear model 20 illustrated in FIG. 1. As illustrated in FIG. 8, the ear model 20b according to the second example embodiment further includes two air pressure control units 203 in addition to the plurality of plate-shaped members 201 and one artificial eardrum member 202. FIG. 8 does not illustrate an auricle model on the ear model 20b.

As illustrated in FIG. 8, the plurality of plate-shaped members 201 are arranged on both upper and lower sides of the artificial eardrum member 202 with the artificial eardrum member 202 interposed therebetween in the ear model 20b. Holes of the plurality of plate-shaped members 201 on the upper side of the artificial eardrum member 202 simulate an external auditory canal of an individual. On the other hand, holes of the plurality of plate-shaped members 201 on the lower side of the artificial eardrum member 202 simulate a middle ear cavity of an individual.

The air pressure control units 203 control the air pressure in a cavity formed in the ear model 20b. The air pressure control unit 203 is an example of an air pressure control means. For example, the air pressure control unit 203 includes a valve inserted into the plate-shaped member 201, a compressor that sends air into a cavity formed in the ear model 20b, a pressure gauge that measures the air pressure in the cavity formed in the ear model 20b, and a pipe configured to send air.

One of the air pressure control units 203 controls the air pressure in a space formed by the holes of the plurality of plate-shaped members 201 on the upper side of the artificial eardrum member 202, that is, the space simulating the external auditory canal of the individual. The other air pressure control unit 203 controls the air pressure in a space formed by the holes of the plurality of plate-shaped members 201 on the lower side of the artificial eardrum member 202, that is, the space simulating the middle ear cavity of the individual. For example, the two air pressure control units 203 perform control such that the air pressure in the space simulating the external auditory canal of the individual is high (low) and the air pressure in the space simulating the middle ear cavity of the individual is low (high). As a result, for example, a low pressure in the high ground or the sky or a high pressure in the water can be reproduced in the ear model 20b.

Effects of Present Example Embodiment

According to the configuration of the present example embodiment, the plurality of plate-shaped members 201 are provided with holes, the artificial eardrum member 202 is equivalent to an eardrum of an individual, and the holes, each of which is provided in each of the plurality of plate-shaped members 201, are connected, whereby the plurality of plate-shaped members 201 are stacked on the artificial eardrum member 202 so as to simulate an external auditory canal of the individual. The earphone device 30 is attached to the ear model 20b, and in-ear acoustic authentication is tried to evaluate performance of the earphone device 30. The ear models 20b having various parameters (R, n) can be easily obtained by changing sizes of diameters of the holes provided in the plurality of plate-shaped members 201 and arrangement orders of the plurality of plate-shaped members 201. As a result, it is possible to easily and inexpensively evaluate the performance of the earphone device 30 to be used for the in-ear acoustic authentication.

Furthermore, the air pressure in the cavity formed in the ear model 20b is controlled by the air pressure control unit 203 according to the configuration of the present example embodiment. As a result, it is possible to evaluate the performance of the earphone device 30 under various environments.

Third Example Embodiment

A third example embodiment will be described with reference to FIG. 9.

(Ear Model 20c)

Figure 9:
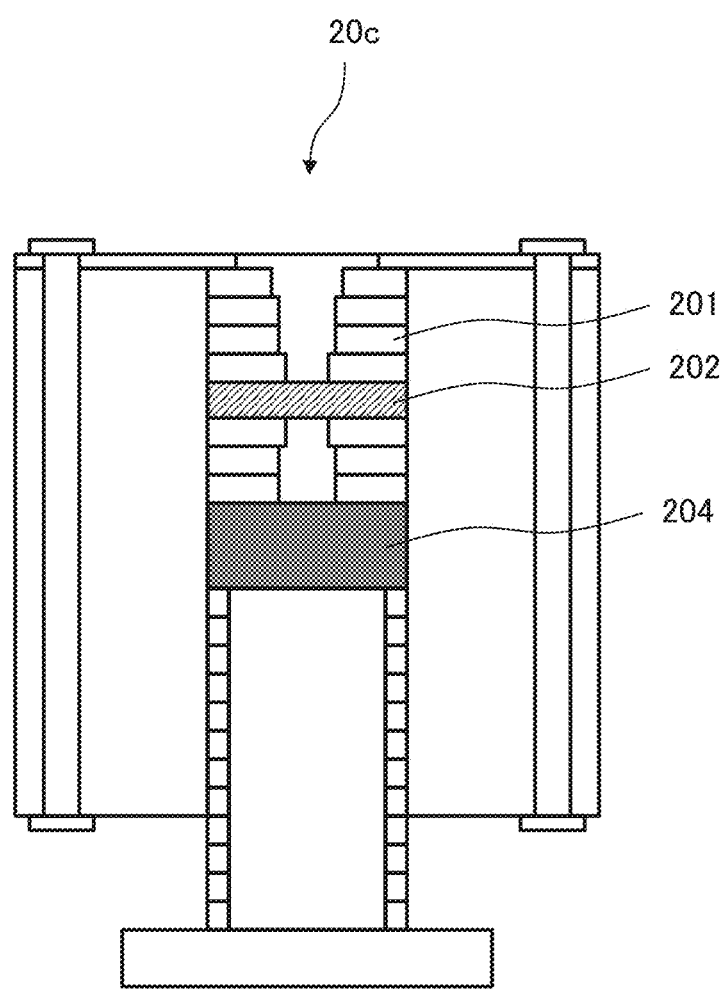
FIG. 9 is a cross-sectional view of an ear model according to a third example embodiment.

FIG. 9 is a cross-sectional view of an ear model 20c which is an example of the ear model 20 illustrated in FIG. 1. As illustrated in FIG. 9, the ear model 20c according to the third example embodiment further includes an artificial muscle member 204 in addition to the plurality of plate-shaped members 201 and one artificial eardrum member 202. FIG. 9 does not illustrate an auricle model on the ear model 20c.

The artificial muscle member 204 is equivalent to a muscle in a vocal tract of an individual. The artificial muscle member 204 is a type of actuator that simulates a structure and properties of the muscle in the vocal tract of the individual. The artificial muscle member 204 is made of, for example, a polymer such as a synthetic resin. Alternatively, the artificial muscle member 204 may be made of a shape memory alloy, a hydrogel, or the like.

The artificial muscle member 204 responds to vibration of air generated in a cavity in the ear model 20c. In other words, the artificial muscle member 204 converts the vibration of air into elastic energy. As a result, it is possible to reproduce tremor of the vocal tract when sound is generated in an ear hole. Furthermore, the interaction between the sound and the tremor of the vocal tract can be reproduced.

In the ear model 20c according to the third example embodiment, the plurality of plate-shaped members 201 are arranged vertically with the artificial eardrum member 202 interposed therebetween, which is similar to the ear model 20b according to the second example embodiment. Holes of the plurality of plate-shaped members 201 on the upper side of the artificial eardrum member 202 simulate an external auditory canal of an individual. Holes of the plurality of plate-shaped members 201 on the lower side of the artificial eardrum member 202 and on the upper side of the artificial muscle member 204 simulate a middle ear cavity of an individual.

The holes of the plurality of plate-shaped members 201 on the lower side of the artificial muscle member 204 simulate the vocal tract of the individual. That is, the ear model 20c simulates an internal structure from an external auditory canal opening (portion connected to an auricle) to the vocal tract in the ear hole of the individual.

Effects of Present Example Embodiment

According to the configuration of the present example embodiment, the plurality of plate-shaped members 201 are provided with holes, the artificial eardrum member 202 is equivalent to an eardrum of an individual, and the holes, each of which is provided in each of the plurality of plate-shaped members 201, are connected, whereby the plurality of plate-shaped members 201 are stacked on the artificial eardrum member 202 so as to simulate an external auditory canal of the individual. The earphone device 30 is attached to the ear model 20c, and in-ear acoustic authentication is tried to evaluate performance of the earphone device 30. The ear models 20c having various parameters (R, n) can be easily obtained by changing sizes of diameters of the holes provided in the plurality of plate-shaped members 201 and arrangement orders of the plurality of plate-shaped members 201. As a result, it is possible to easily and inexpensively evaluate the performance of the earphone device 30 to be used for the in-ear acoustic authentication.

Furthermore, the artificial muscle member 204 is equivalent to the muscle in the vocal tract of the individual according to the configuration of the present example embodiment. The vibration of the artificial muscle member 204 reproduces the tremor of the vocal tract of the individual when the sound is generated in the ear hole. As a result, it is possible to more precisely evaluate the performance of the earphone device 30.

[Hardware Configuration]

Figure 10:
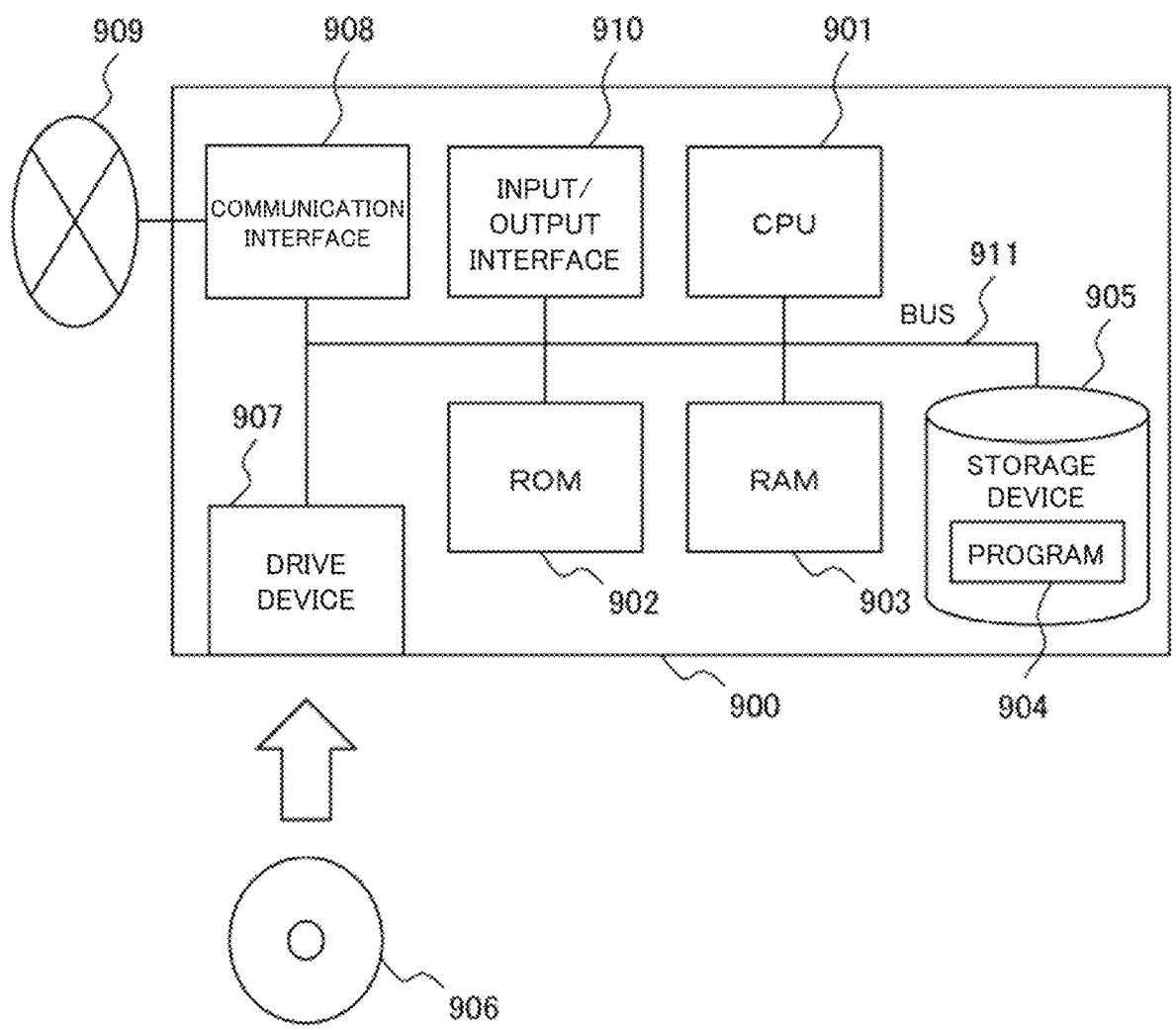
FIG. 10 is a diagram illustrating a hardware configuration of the computing device according to any one of first to third example embodiments.

Each of components of the computing device 10 described in the first to third example embodiments indicates a block of a functional unit. Some or all of these components are implemented by an information processing device 900 as illustrated in FIG. 10, for example. FIG. 10 is a block diagram illustrating an example of a hardware configuration of the information processing device 900.

As illustrated in FIG. 10, the information processing device 900 includes the following configuration as an example.

A central processing unit (CPU) 901
A read only memory (ROM) 902
A random access memory (RAM) 903
A program 904 to be loaded into the RAM 903
A storage device 905 storing the program 904
A drive device 907 performing read and write with respect to a recording medium 906
A communication interface 908 connected to a communication network 909
An input/output interface 910 performing input/output of data
A bus 911 connecting components Each of the components of the computing device 10 described in the first to third example embodiments is implemented as the CPU 901 reads and executes the program 904 for implementing these functions. The program 904 for implementing the functions of the components is stored in the storage device 905 or the ROM 902 in advance, for example, and is loaded into the RAM 903 and executed by the CPU 901. Note that the program 904 may be supplied to the CPU 901 through the communication network 909, or may be stored in advance in the recording medium 906, and the drive device 907 may read the program and supply the program to the CPU 901.

Effects of Present Example Embodiment

According to the configuration of the present example embodiment, the computing device 10 described in the above example embodiments is implemented as hardware. Therefore, effects similar to the effects described in the first to third example embodiments can be obtained.

While the invention has been particularly shown and described with reference to exemplary embodiments thereof, the invention is not limited to these embodiments. It will be understood by those of ordinary skill in the art that various changes in form and details may be made therein without departing from the spirit and scope of the present invention as defined by the claims.

(Supplementary Notes)

Some or all of the above example embodiments may be described as the following supplementary notes, but are not limited to the following.

(Supplementary Note 1)

An ear model including:
a plurality of plate-shaped members provided with holes; and an artificial eardrum member equivalent to an eardrum of an individual,
wherein the holes, each of which is provided in each of the plurality of plate-shaped members, are connected, whereby the plurality of plate-shaped members are stacked on the artificial eardrum member in such a way as to simulate an external auditory canal of the individual.

(Supplementary Note 2)

The ear model according to Supplementary Note 1, wherein
a thickness and a number of the plurality of plate-shaped members are related to a length from an external auditory canal opening to the eardrum of the individual.

(Supplementary Note 3)

The ear model according to Supplementary Note 1 or 2, wherein
a diameter of the hole provided in each of the plurality of plate-shaped members is related to a thickness of the external auditory canal of the individual.

(Supplementary Note 4)

The ear model according to any one of Supplementary Notes 1 to 3, further including
an air pressure control means configured to control air pressure in a cavity formed in the ear model as the holes, each of which is provided in each of the plurality of plate-shaped members, are connected.

(Supplementary Note 5)

The ear model according to any one of Supplementary Notes 1 to 4, wherein
the holes, each of which is provided in each of the plurality of plate-shaped members, are connected, whereby the plurality of plate-shaped members are stacked on both sides of the artificial eardrum member with the artificial eardrum member interposed between the plate-shaped members in such a way as to simulate the external auditory canal and a middle ear cavity of the individual.

(Supplementary Note 6)

The ear model according to any one of Supplementary Notes 1 to 5, further including
an artificial muscle member equivalent to a muscle in a vocal tract of the individual,
wherein the holes, each of which is provided in each of the plurality of plate-shaped members, are connected, whereby the plurality of plate-shaped members are stacked between the artificial muscle member and the artificial eardrum member in such a way as to simulate the vocal tract of the individual.

(Supplementary Note 7)

A performance evaluation method being a method for evaluating performance of an earphone device to be used for in-ear acoustic authentication using the ear model according to any one of Supplementary Notes 1 to 6, the performance evaluation method including:
transmitting an inspection signal from the earphone device toward a site of the ear model equivalent to an external auditory canal opening of the individual;
collecting echo sound, transmitted from the ear model after the inspection signal propagates in the ear model, using the earphone device;
calculating an acoustic characteristic of the ear model from an echo signal based on the collected echo sound; and
evaluating performance of the earphone device based on the acoustic characteristic.

(Supplementary Note 8)

The performance evaluation method according to Supplementary Note 7, wherein
the earphone device that is identical is repeatedly attached to and detached from the ear model, and
the acoustic characteristic is calculated every time the identical earphone device is attached to and detached from the ear model, and
first performance of the identical earphone device is evaluated based on a variance of the repeatedly calculated acoustic characteristics.

(Supplementary Note 9)

The performance evaluation method according to Supplementary Note 7 or 8, wherein
the acoustic characteristic is calculated for each of a plurality of the ear models having different shapes,
pieces of acoustic characteristic data in which parameters, each of which represents the shapes of the plurality of ear models, are associated with the acoustic characteristics of the plurality of ear models are accumulated; and
second performance of the earphone device is evaluated based on a variance of the acoustic characteristics among the plurality of ear models.

(Supplementary Note 10)

The performance evaluation method according to Supplementary Note 9, wherein
the parameter is at least one of a number of the plurality of plate-shaped members related to a length from the external auditory canal opening to the eardrum of the individual and a size of a diameter of the hole related to a thickness of the external auditory canal of the individual.

(Supplementary Note 11)

A performance evaluation system including:
the ear model according to any one of Supplementary Notes 1 to 6;
an earphone device that transmits an inspection signal toward a site of the ear model equivalent to an external auditory canal opening of the individual and observes an echo signal based on an echo sound transmitted from the ear model after the inspection signal propagates in the ear model; and
a computing device that calculates an acoustic characteristic of the ear model from the echo signal based on the echo sound that has been collected and calculates an index value indicating performance of the earphone device based on the acoustic characteristic.

REFERENCE SIGNS LIST 1 performance evaluation system
20 (20a to 20c) ear model
30 earphone device
201 plate-shaped member
202 artificial eardrum member
203 air pressure control unit
204 artificial muscle member

What is claimed is:
1. An ear model comprising:
a plurality of plate-shaped members provided with holes; and
an artificial eardrum member equivalent to an eardrum of an individual,
wherein the holes, each of which is provided in each of the plurality of plate-shaped members, are connected, whereby the plurality of plate-shaped members are stacked on the artificial eardrum member in such a way as to simulate an external auditory canal of the individual, wherein the ear model is configured to reproduce a J value, indicating an acoustic characteristic of an internal structure of an ear hole of an individual, by using two parameters (R, n) being a size (R) of diameter of a hole in each of the plurality of plate-shaped members and arrangement order (n) of the plurality of plate-shaped members.

2. The ear model according to claim 1, wherein a thickness and a number of the plurality of plate-shaped members are related to a length from an external auditory canal opening to the eardrum of the individual.

3. The ear model according to claim 1, wherein a diameter of the hole provided in each of the plurality of plate-shaped members is related to a thickness of the external auditory canal of the individual.

4. The ear model according to claim 1, further comprising;
a memory configured to store instructions data; and
at least one processors configured to execute the instructions to perform:
controlling air pressure in a cavity formed in the ear model as the holes, each of which is provided in each of the plurality of plate-shaped members are connected.

5. The ear model according to claim 1, wherein the holes, each of which is provided in each of the plurality of plate-shaped members, are connected, whereby the plurality of plate-shaped members are stacked on both sides of the artificial eardrum member with the artificial eardrum member interposed between the plate-shaped members in such a way as to simulate the external auditory canal and a middle ear cavity of the individual.

6. The ear model according to claim 1, further comprising an artificial muscle member equivalent to a muscle in a vocal tract of the individual,
wherein the holes, each of which is provided in each of the plurality of plate-shaped members, are connected, whereby the plurality of plate-shaped members are stacked between the artificial muscle member and the artificial eardrum member in such a way as to simulate the vocal tract of the individual.

7. A performance evaluation method being a method for evaluating performance of an earphone device to be used for in-ear acoustic authentication using the ear model according to claim 1, the performance evaluation method comprising:
transmitting an inspection signal from the earphone device toward a site of the ear model equivalent to an external auditory canal opening of the individual;
collecting echo sound, transmitted from the ear model after the inspection signal propagates in the ear model, using the earphone device;
calculating an acoustic characteristic of the ear model from an echo signal based on the collected echo sound; and
evaluating performance of the earphone device based on the acoustic characteristic,
wherein the performance evaluation method further comprises making the ear model configured to reproduce J value, indicating an acoustic characteristic of an internal structure of an ear hole of an individual, by using two parameters (R, n) being a size (R) of diameter of a hole in each of the plurality of plate-shaped members and arrangement order (n) of the plurality of plate-shaped members.

8. The performance evaluation method according to claim 7, wherein
the earphone device that is identical is repeatedly attached to and detached from the ear model, and
the acoustic characteristic is calculated every time the identical earphone device is attached to and detached from the ear model, and
first performance of the identical earphone device is evaluated based on a variance of the repeatedly calculated acoustic characteristics.

9. The performance evaluation method according to claim 7, wherein
the acoustic characteristic is calculated for each of a plurality of the ear models having different shapes,
pieces of acoustic characteristic data in which parameters, each of which represents each of the shapes of the plurality of ear models, are associated with the acoustic characteristics of the plurality of ear models are accumulated; and
second performance of the earphone device is evaluated based on a variance of the acoustic characteristics among the plurality of ear models.

10. The performance evaluation method according to claim 9, wherein
the parameter is at least one of a number of the plurality of plate-shaped members related to a length from the external auditory canal opening to the eardrum of the individual and a size of a diameter of the hole related to a thickness of the external auditory canal of the individual.

11. A performance evaluation system comprising:
the ear model according to claim 1;
an earphone device that transmits an inspection signal toward a site of the ear model equivalent to an external auditory canal opening of the individual and collects an echo sound transmitted from the ear model after the inspection signal propagates in the ear model; and
a computing device that calculates an acoustic characteristic of the ear model from an echo signal based on the collected echo sound and calculates an index value indicating performance of the earphone device based on the acoustic characteristic.

* * * * *